(12) United States Patent
Komiya et al.

(10) Patent No.: US 10,595,931 B2
(45) Date of Patent: Mar. 24, 2020

(54) LIQUID FEEDER AND TREATMENT APPARATUS

(71) Applicant: OLYMPUS CORPORATION, Hachioji-shi, Tokyo (JP)

(72) Inventors: Mizuki Komiya, Hachioji (JP); Kazunori Taniguchi, Hamburg (DE)

(73) Assignee: OLYMPUS CORPORATION, Tokyo (JP)

( * ) Notice: Subject to any disclaimer, the term of this patent is extended or adjusted under 35 U.S.C. 154(b) by 499 days.

(21) Appl. No.: 15/404,797

(22) Filed: Jan. 12, 2017

(65) Prior Publication Data
US 2017/0119451 A1 May 4, 2017

Related U.S. Application Data

(63) Continuation of application No. PCT/JP2015/062866, filed on Apr. 28, 2015.

(30) Foreign Application Priority Data

Jul. 15, 2014 (JP) ................................. 2014-145308

(51) Int. Cl.
*A61B 18/04* (2006.01)
*A61B 18/14* (2006.01)
(Continued)

(52) U.S. Cl.
CPC .. *A61B 18/1445* (2013.01); *A61B 17/320092* (2013.01); *A61B 2017/2929* (2013.01);
(Continued)

(58) Field of Classification Search
CPC ... A61B 18/04; A61B 18/042; A61B 18/1442; A61B 18/1445; A61B 18/085;
(Continued)

(56) References Cited

U.S. PATENT DOCUMENTS 4,425,115 A * 1/1984 Wuchinich ....... A61B 17/22004
310/26
5,085,657 A 2/1992 Ben-Simhon
(Continued)

FOREIGN PATENT DOCUMENTS

EP 2601901 A1 6/2013
JP H03-151954 A 6/1991
(Continued)

OTHER PUBLICATIONS

Jul. 28, 2015 International Search Report issued in International Patent Application No. PCT/JP2015/062866.
(Continued)

*Primary Examiner* — Thomas A Giuliani
(74) *Attorney, Agent, or Firm* — Oliff PLC

(57) ABSTRACT

A liquid feeder mounted on a treatment instrument, includes: a main tube that is arranged along a long member of the treatment instrument in which a longitudinal axis is defined and that is configured to flow a liquid to an outer circumference of the long member; a connection section that is arranged on a proximal end side of the main tube along the longitudinal axis and that is configured to connect an interior of the main tube and an interior of a liquid feed channel from a liquid source; and a fixing section that is arranged in the connection section and that is configured to fix the connection section to a handle unit arranged at a proximal end of the long member and grasped by a user.

10 Claims, 14 Drawing Sheets

(51) Int. Cl.
*A61B 17/32* (2006.01)
*A61B 17/29* (2006.01)
*A61B 18/00* (2006.01)

(52) U.S. Cl.
CPC .............. *A61B 2017/320069* (2017.08); *A61B 2017/320084* (2013.01); *A61B 2017/320094* (2017.08); *A61B 2017/320095* (2017.08); *A61B 2018/00029* (2013.01); *A61B 2018/00994* (2013.01); *A61B 2218/002* (2013.01)

(58) Field of Classification Search
CPC ...... A61B 2018/122; A61B 2018/1472; A61B 2018/00994; A61B 2018/0063; A61B 2018/00589; A61B 2018/00005; A61B 2018/00011; A61B 2018/00029; A61B 2018/00202; A61B 2218/002; A61B 17/320092; A61B 17/320068; A61B 17/22012; A61B 2017/22011; A61B 2017/2929; A61B 2017/320069; A61B 2017/320071; A61B 2017/320074; A61B 2017/320082; A61B 2017/320084; A61B 2017/320093; A61B 2017/320094; A61B 2017/320095; A61N 7/02
USPC ................................ 606/20–52; 607/104–107
See application file for complete search history.

(56) References Cited

U.S. PATENT DOCUMENTS

2006/0265035 A1* 11/2006 Yachi ............... A61B 17/32009
607/101
2011/0224662 A1* 9/2011 Toubia .................. A61B 18/02
606/23
2013/0079751 A1 3/2013 Dexter et al.

FOREIGN PATENT DOCUMENTS

JP 2006-341066 A 12/2006
JP 2008-093019 A 4/2008

OTHER PUBLICATIONS

Feb. 23, 2016 Office Action issued in Japanese Patent Application No. 2016-500012.
May 17, 2016 Office Action issued in Japanese Patent Application No. 2016-500012.
Aug. 16, 2016 Office Action issued in Japanese Patent Application No. 2016-500012.
Jan. 17, 2017 International Preliminary Report on Patentability issued in International Patent Application No. PCT/ JP2015/ 062866.
Jan. 29, 2018 Extended European Search Report issued in European Patent Application No. 15822824.7.

* cited by examiner

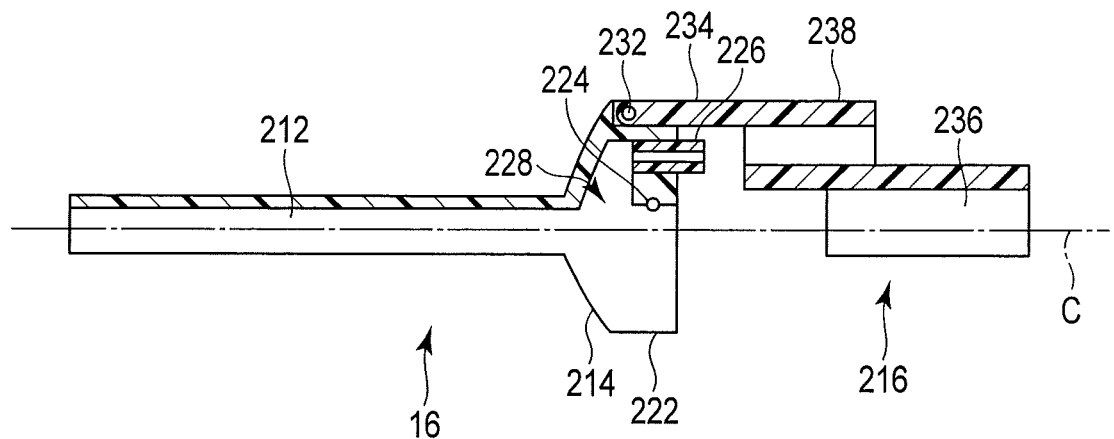
F I G. 6
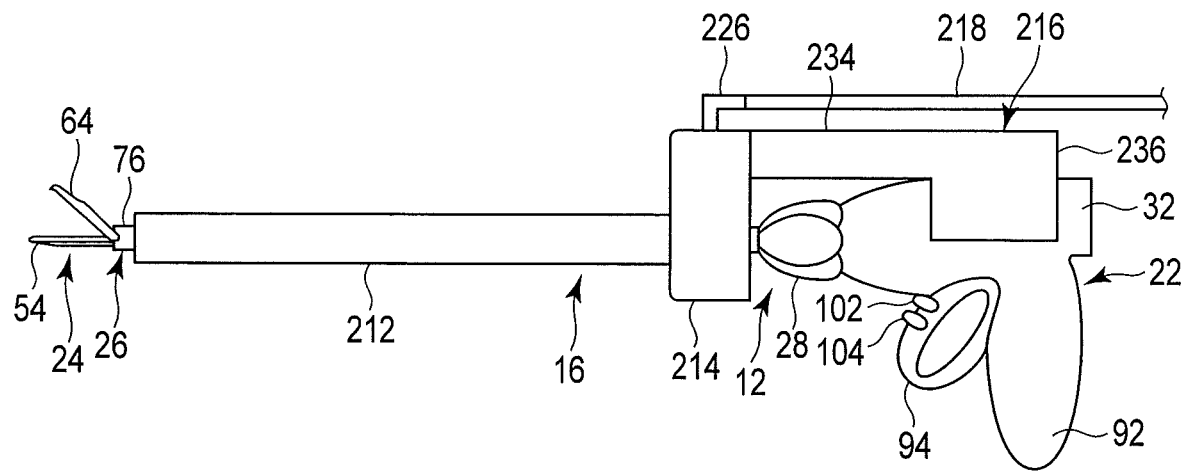
F I G. 7

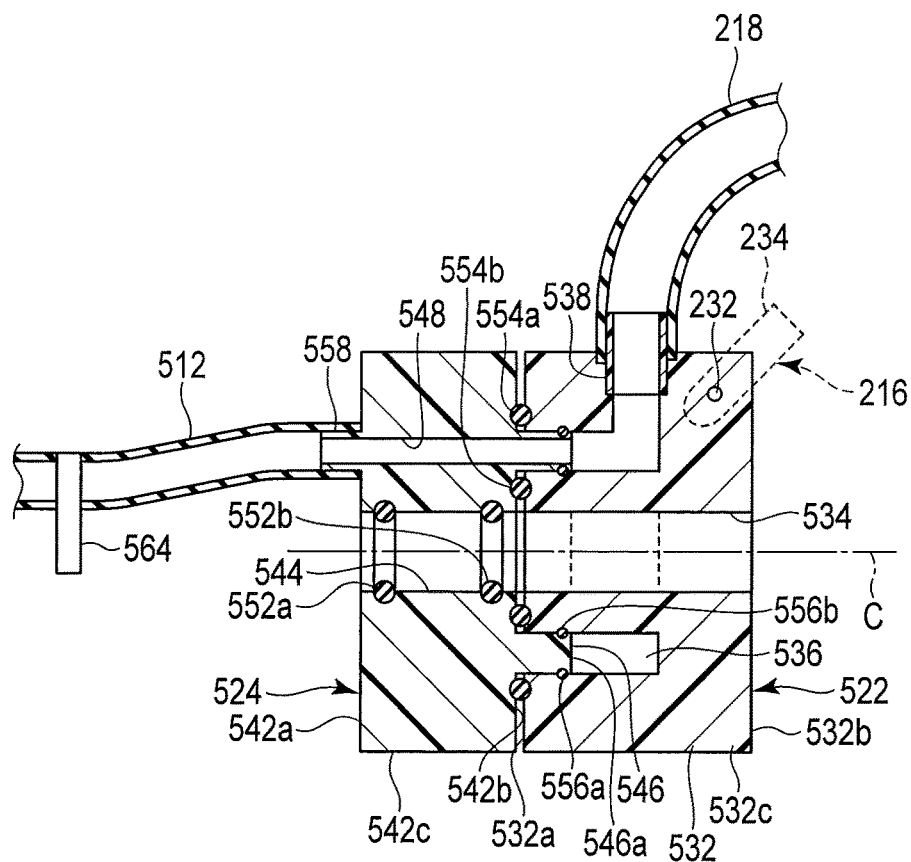
F I G. 18A
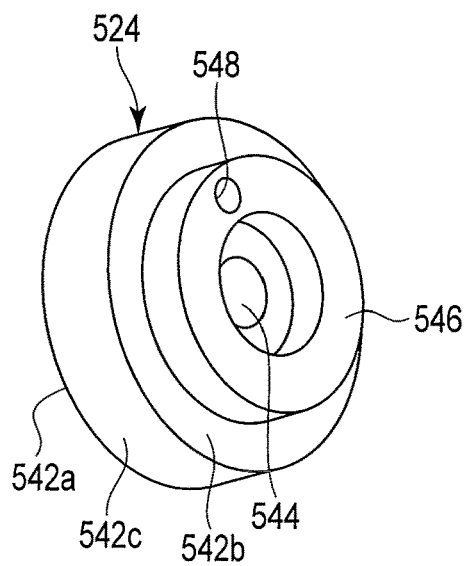
F I G. 18B

LIQUID FEEDER AND TREATMENT APPARATUS

CROSS-REFERENCE TO RELATED APPLICATIONS

This application is a Continuation Application of PCT Application No. PCT/JP2015/062866, filed Apr. 28, 2015 and based upon and claiming the benefit of priority from prior Japanese Patent Application No. 2014-145308, filed Jul. 15, 2014, the entire contents of all of which are incorporated herein by reference.

BACKGROUND OF THE INVENTION

1. Field of the Invention

This invention relates to a liquid feeder mounted on a treatment instrument, and a treatment apparatus including the liquid feeder and the treatment instrument.

2. Description of the Related Art

For example, U.S. Patent Application Publication No. 2006/0265035 discloses a treatment instrument for treating a tissue by an ultrasonic vibration. This treatment instrument can rotate a sheath unit (long member) by the rotation of a knob. Furthermore, this treatment instrument can externally attach/detach, to/from the sheath unit, a liquid feeder capable of supplying a liquid such as physiological saline to a treatment section (the distal end of the sheath unit) through a liquid feed tube.

BRIEF SUMMARY OF THE INVENTION

According to one aspect of the present invention, a liquid feeder mounted on a treatment instrument, includes: a main tube that is arranged along a long member of the treatment instrument in which a longitudinal axis is defined and that is configured to flow a liquid to an outer circumference of the long member; a connection section that is arranged on a proximal end side of the main tube along the longitudinal axis and that is configured to connect an interior of the main tube and an interior of a liquid feed channel from a liquid source; and a fixing section that is arranged in the connection section and that is configured to fix the connection section to a handle unit arranged at a proximal end of the long member and grasped by a user.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a partial longitudinal sectional view showing the liquid feeder of the surgical operation system according to the first embodiment.

FIG. 7 is a schematic view showing the surgical treatment instrument and liquid feeder of the surgical operation system according to the first modification of the first embodiment, and showing a state in which the liquid feeder is attached to the surgical treatment instrument.

FIG. 18A is a schematic longitudinal sectional view showing the liquid feeder of the surgical operation system according to the first embodiment.

FIG. 18B is a schematic perspective view showing a rotation adapter shown in FIG. 18A.

DETAILED DESCRIPTION OF THE INVENTION

Embodiments of the present invention, will be described below with reference to the accompanying drawings.

The first embodiment will be described with reference to FIGS. 1A to 6.

Figure 1A:
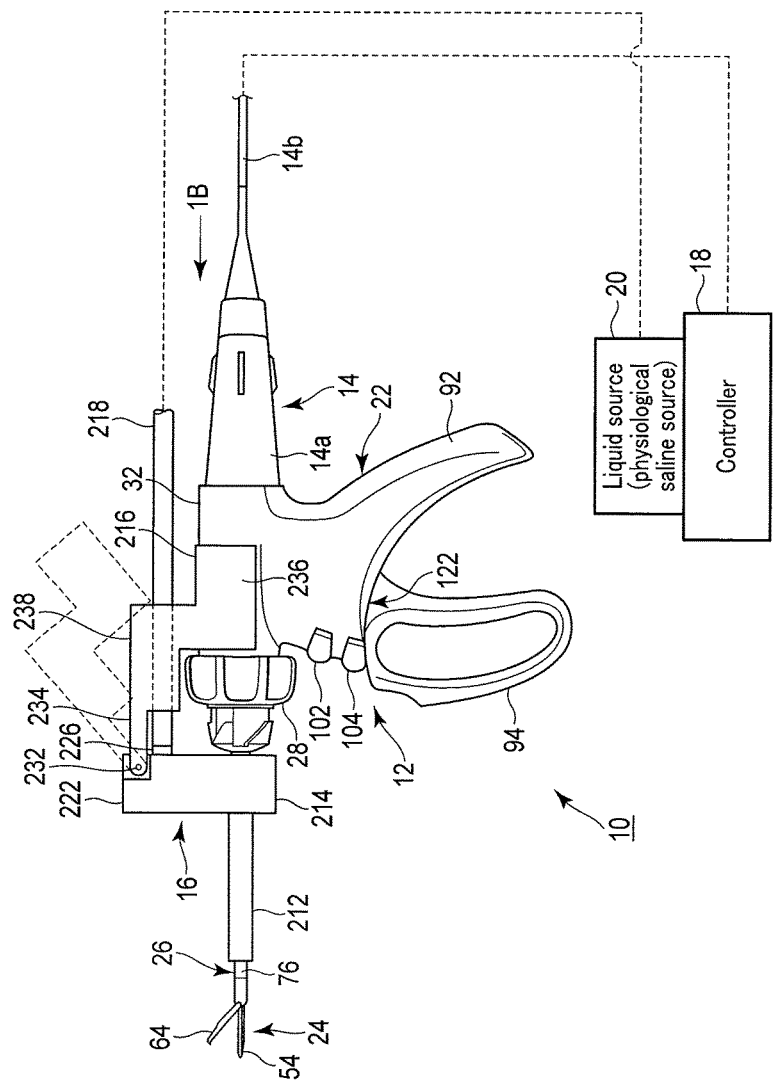
FIG. 1A is a schematic view showing a surgical operation system according to the first embodiment.

As shown in FIG. 1A, a surgical operation system (treatment apparatus) 10 according to this embodiment includes a surgical treatment instrument (surgical operation device) 12, an ultrasonic transducer unit 14, a liquid feeder (water feeder) 16, and a controller 18. The surgical treatment instrument 12 and the liquid feeder 16 are used in combination. This surgical operation system 10 further includes a liquid source 20 for supplying a liquid such as physiological saline to the liquid feeder 16.

This embodiment will be explained by assuming that the surgical treatment instrument 12 is a treatment instrument capable of treating a tissue by an ultrasonic vibration or capable of treating a tissue using high-frequency energy in addition to an ultrasonic vibration.

The surgical treatment instrument 12 includes a handle unit 22 for performing various kinds of treatment by operating an end effector (to be described later), a probe (long member) 24, a sheath unit (long member) 26, and a rotation knob 28. The handle unit 22 (an exterior case 32 (to be described later)) has a center axis C. For example, the transducer unit 14, the probe 24, the sheath unit 26, and the rotation knob 28 are connected to the handle unit 22 on the center axis C.

Figure 1B:
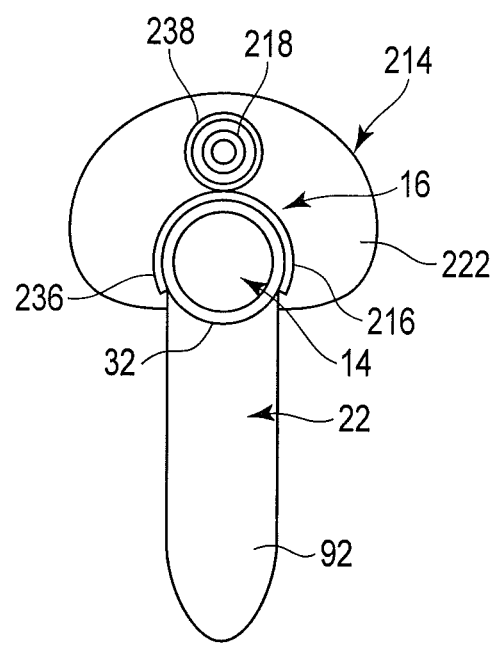
FIG. 1B is a schematic view showing a state when a surgical treatment instrument and a liquid feeder are viewed from the direction of an arrow 1B in FIG. 1A.
Figure 2:
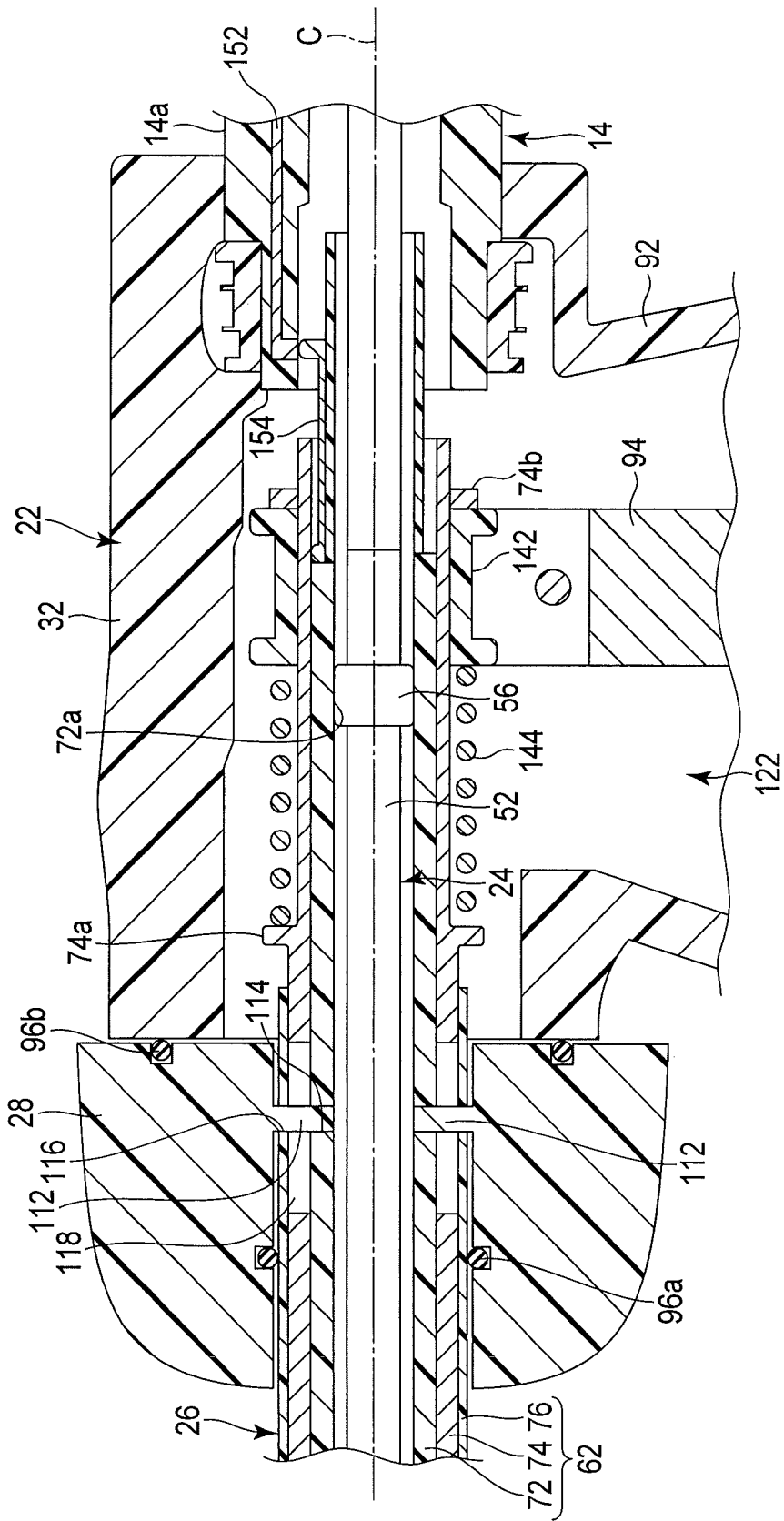
FIG. 2 is a schematic longitudinal sectional view showing the distal end of a transducer unit, a probe main body, the proximal end of a sheath unit, and the connection section of a handle unit.

As shown in FIGS. 1B and 2, the handle unit 22 for the surgical treatment instrument 12 includes the cylindrically formed exterior case (handle main body) 32. The exterior case 32 is preferably made of a hard plastic material having an electrical insulating property and heat resistance. As shown in FIG. 2, the probe 24 and the transducer unit 14 disposed on the proximal end side of the probe 24 are supported in the exterior case 32.

Figure 3:
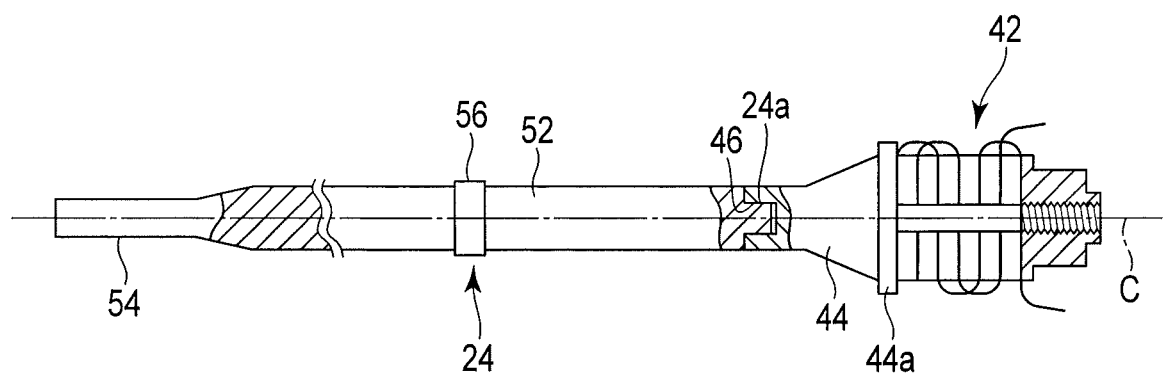
FIG. 3 is a schematic partial sectional view showing the ultrasonic transducer unit of the surgical treatment instrument and a probe connected to the transducer unit according to the first embodiment.

As shown in FIG. 3, the transducer unit 14 includes an ultrasonic transducer 42 for generating an ultrasonic vibration by being appropriately supplied with power from the controller 18 (see FIG. 1A), and a cone-shaped horn 44 for enlarging the amplitude of the ultrasonic vibration generated by the ultrasonic transducer 42. The ultrasonic transducer 42 and the horn 44 are arranged inside a cylindrical transducer case 14a having an electrical insulating property shown in FIG. 1A. The horn 44 is attached to an external thread 24a at the proximal end of the probe 24 by a connection thread (internal thread) 46. The horn 44 includes an outer flange 44a projecting radially outward with respect to the center axis C of the horn 44. The outer flange 44a is supported by the transducer case 14a.

This embodiment assumes that the ultrasonic transducer unit 14 is detachably supported by the exterior case 32. However, it is also preferable that the ultrasonic transducer unit 14 is fixed to the exterior case 32.

A cable 14b is connected to the proximal end side of the transducer case 14a. The cable 14b can transmit/receive a signal to/from the controller 18 shown in FIG. 1A by a switch 102 or 104 (to be described later) or the like, appropriately supply power to the ultrasonic transducer 42 based on the signal input to the controller 18, and appropriately supply power to the probe 24 and a jaw 64 (to be described later) based on the signal input to the controller 18. Furthermore, the controller 18 can control an adjustment section (not shown) such as a valve for adjusting the flow rate per unit time of physiological saline which flows from the liquid source 20 to the liquid feeder 16. A fluid may be supplied from the liquid source 20 to the liquid feeder 16 by a pump (not shown), or a fluid may be supplied by gravity by arranging the liquid source 20 at a position higher than that of the liquid feeder 16.

The probe 24 shown in FIG. 3 is designed so that the total length (the length along the center axis C) is an integer multiple of the half-wave length of the ultrasonic vibration. The probe 24 includes a rod-shaped probe main body 52 made of metal such as a titanium alloy, and a treatment section 54 provided on the distal end side of the probe main body 52. The ultrasonic vibration generated by the ultrasonic transducer 42 is enlarged in amplitude by the horn 44, and transferred to the treatment section 54 via the probe main body 52.

A positioning section 56 which is prevented from rotating with respect to an inner sheath 72 (to be described later) is formed on the outer circumferential surface of the probe main body 52. The positioning section 56 is formed into a shape other than a circle. The positioning section 56 is preferably arranged in the axial direction at the node position of the vibration. Note that the movement of the positioning section 56 to the distal end side along the center axis C with respect to the inner sheath 72 is restricted.

Figure 4:
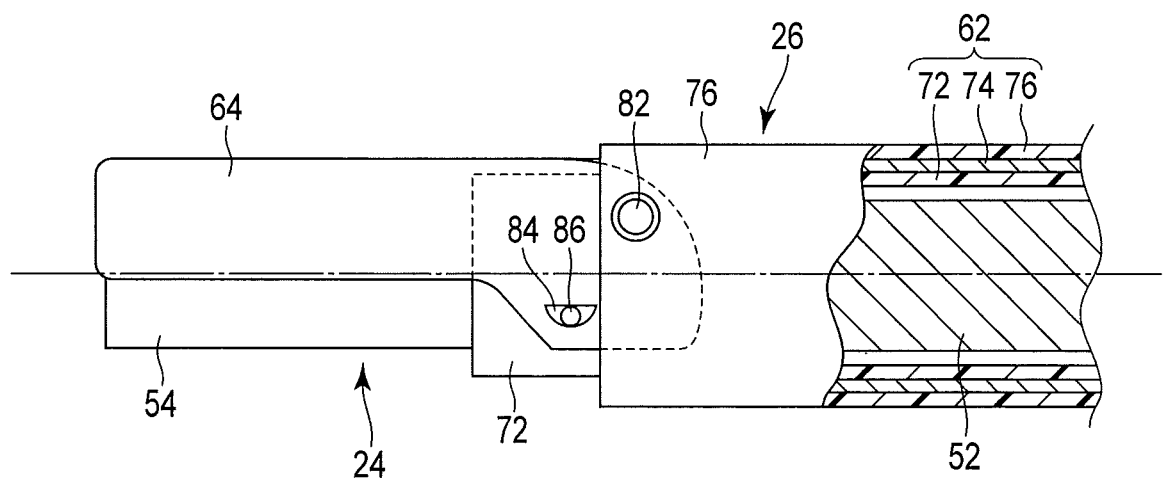
FIG. 4 is a partial sectional view showing the arrangement of the treatment section of the probe and the jaw of the surgical treatment instrument according to the first embodiment.

As shown in FIG. 4, the sheath unit 26 includes a cylindrical sheath main body 62, and the jaw 64 serving as an end effector disposed on the distal end side of the sheath main body 62. The sheath main body 62 includes the cylindrical inner sheath 72 serving as an inner cylinder, a cylindrical driving pipe (driving member) 74, and a cylindrical outer sheath 76 serving as an outer cylinder. The driving pipe 74 is disposed to be slidable in the axial direction of the center axis C outside the inner sheath 72. The probe 24 is inserted into the inner sheath 72. That is, the probe 24 can transfer the ultrasonic vibration, and the outer circumference of the probe 24 is covered with the sheath unit 26.

Note that the inner sheath 72 and the outer sheath 76 are made of a material having an electrical insulating property and heat resistance, such as a PTFE material. In this embodiment, the driving pipe 74 is made of a conductive material.

The proximal end of the jaw 64 is pivotably supported by a fulcrum pin 82 at the distal end of the inner sheath 72.

When assembling the probe 24 and the sheath unit 26, the jaw 64 is arranged at a position facing the treatment section 54 of the probe 24. The jaw 64 can come into contact with and move away from the treatment section 54 at the distal end of the probe 24.

Note that a fitting section 72a in which the positioning section 56 of the probe 24 is fitted is formed on the inner circumferential surface of the inner sheath 72. The fitting section 72a restricts the movement of the probe 24 to the distal end side along the center axis C with respect to the inner sheath 72.

The jaw 64 includes connecting pin supports 84 on the two sides of its proximal end section near the fulcrum pin 82. A connecting pin 86 for connecting the jaw 64 and the driving pipe 74 is mounted on each connecting pin support 84. When the driving pipe 74 performs back-and-forth movement in the axial direction, the driving force of the driving pipe 74 is transferred to the jaw 64 via the connecting pins 86. Thus, the jaw 64 is pivoted about the fulcrum pin 82. Then, the jaw 64 moves closer to and away from the treatment section 54. That is, the jaw 64 is opened/closed. At this time, if the driving pipe 74 is moved to the proximal end side, the jaw 64 moves away from the treatment section 54, that is, moves in an opening direction. If the driving pipe 74 moves to the distal end side, the jaw 64 moves closer to the treatment section 54, that is, moves in a closing direction.

Note that the connecting pins 86 are made of a conductive material. Part of the jaw 64 is made of a conductive material. Therefore, the driving pipe 74 and the jaw 64 are electrically connected.

As shown in FIG. 1A, the handle unit 22 includes a stationary handle (fixing member) 92, and a movable handle (moving member) 94 movable with respect to the stationary handle 92. The rotation knob 28 capable of rotating the probe 24 and the sheath unit 26 about the center axis C is disposed at the distal end of the handle unit 22.

As shown in FIG. 2, the stationary handle 92 is formed integrally with the exterior case (handle main body) 32, or fixed to the exterior case 32. A plurality of switches (the upper switch 102 and the lower switch 104) are arranged on the distal end face (front face) of the exterior case 32.

FIG. 2 shows the distal end of the transducer unit 14, the probe main body 52, the proximal end of the sheath unit 26, and the connection section of the handle unit 22. As shown in FIG. 2, in this embodiment, the rotation knob 28 is attached to the sheath unit 26. The connection structure of the rotation knob 28, the inner sheath 72, the driving pipe 74, and the outer sheath 76 will be briefly explained.

The rotation knob 28 includes, on its inner circumferential surface, a pair of engaging pawls 112 projecting inward. The inner sheath 72 and the outer sheath 76 respectively include a pair of engaging holes 114 and a pair of engaging holes 116 which communicate the interior and the exterior and with which the engaging pawls 112 are engaged. The driving pipe 74 includes a pair of sliding holes 118 which communicate the interior and the exterior and can relatively move the engaging pawls 112. Each sliding hole 118 is formed as a long hole in a direction along the center axis C. When the engaging pawls 112 of the rotation knob 28 are engaged with the engaging holes 114 of the inner sheath 72, the sliding holes 118 of the driving pipe 74, and the engaging holes 116 of the outer sheath 76, the inner sheath 72, the driving pipe 74, and the outer sheath 76 are attached to the rotation knob 28.

The inner sheath 72 and the outer sheath 76 are positioned with respect to the rotation knob 28. The sliding holes 118 of the driving pipe 74 allow the driving pipe 74 to move along the axial direction of the center axis C within a predetermined range with respect to the rotation knob 28. On the other hand, the engaging holes 114 and 116 and the sliding holes 118 cause the inner sheath 72, the driving pipe 74, and the outer sheath 76 to rotate together based on the rotation of the rotation knob 28. That is, the rotation knob 28 arranged between the proximal end of the sheath unit (long member) 26 and the distal end of the handle unit 22 rotates the sheath unit 26 about the center axis (longitudinal axis) C. When pivoting the rotation knob 28 about the center axis C of the sheath unit 26, the probe main body 52 which is prevented from rotating with respect to the inner sheath 72 inside the exterior case 32 integrally rotates about the center axis C together with the rotation knob 28. In synchronism with this operation, the jaw 64 of the sheath unit 26 and the treatment section 54 of the probe 24 also rotate about the center axis C integrally with the inner sheath 72, the driving pipe 74, the outer sheath 76, and the probe main body 52.

That is, it is possible to appropriately adjust the orientations of the jaw 64 and the treatment section 54 of the probe 24 with respect to a treatment target tissue by rotating the rotation knob 28 about the center axis C of the sheath unit 26.

Note that an O-ring 96a is disposed between the inner circumferential surface of the rotation knob 28 and the outer circumferential surface of the outer sheath 76 and an O-ring 96b is disposed between the proximal end of the rotation knob 28 and the distal end of the exterior case 32 of the handle unit 22. Therefore, the O-rings 96a and 96b prevent a liquid from entering the interior of the exterior case 32 of the handle unit 22 from the outer circumferential surface of the sheath unit 26.

As shown in FIG. 1A, the exterior case 32 includes, on the distal end side of the stationary handle 92, an opening 122 which defines the movable range of the movable handle 94. The movable handle 94 has one end inside the exterior case 32 and the other end outside the exterior case 32. The opening 122 defines a pivot range within which the movable handle 94 is made to come into contact with and move away from the stationary handle 92.

The movable handle 94 is arranged at a position far from the stationary handle 92 in the opening 122 while it is not held by the user.

As shown in FIG. 2, the proximal end of the driving pipe 74 projects to the proximal end side of the outer sheath 76 along the center axis C. The proximal end of the inner sheath 72 projects to the proximal end side of the driving pipe 74 along the center axis C.

A pair of outer flanges 74a and 74b projecting radially outward are formed on the outer circumference of the driving pipe 74. A slider 142 movable in the axial direction within a predetermined range is disposed between the outer flanges 74a and 74b. An elastic member 144 formed by, for example, a coil spring is disposed between the slider 142 and the outer flange 74a on the distal end side. Consequently, the slider 142 abuts against the outer flange 74b on the proximal end side by the elastic member 144, and is separated from the outer flange 74a on the distal end side. One end of the movable handle 94 is disposed in the slider 142. At this time, the movable handle 94 is separated from the stationary handle 92.

If, for example, a closing operation is performed to move the movable handle 94 closer to the stationary handle 92, the driving pipe 74 moves to the distal end side along the center axis C by the biasing force of the elastic member 144 along with the movement of the slider 142 to the distal end side along the center axis C. Consequently, the jaw 64 is closed with respect to the treatment section 54 of the probe 24 in synchronism with the movement of the driving pipe 74. On the other hand, for example, if an opening operation is performed to separate the movable handle 94 from the stationary handle 92, the driving pipe 74 moves to the proximal end side along the center axis C by the biasing force of the elastic member 144 along with the movement of the slider 142 to the proximal end side along the center axis C. Consequently, the jaw 64 opens with respect to the treatment section 54 of the probe 24 in synchronism with the movement of the driving pipe 74.

A conducting path 152 through which a current flows when performing high-frequency treatment is formed in the transducer case 14a. A terminal 154 electrically connected to the conducting path 152 of the transducer case 14a of the transducer unit 14 is disposed on the outer circumferential surface of the inner sheath 72. The terminal 154 has a spring property to continuously contact the conducting path 152 while maintaining an electrically connected state with respect to the driving pipe 74 moving along the center axis C. The distal end of the driving pipe 74 is electrically connected to the jaw 64. The jaw 64 is used as one electrode of a bipolar electrode.

On the other hand, the treatment section 54 of the probe 24 is used as the other electrode of the bipolar electrode. A current flows to the horn 44 at the proximal end of the probe 24 through a lead wire (not shown) laid in the transducer case 14a.

Figure 5:
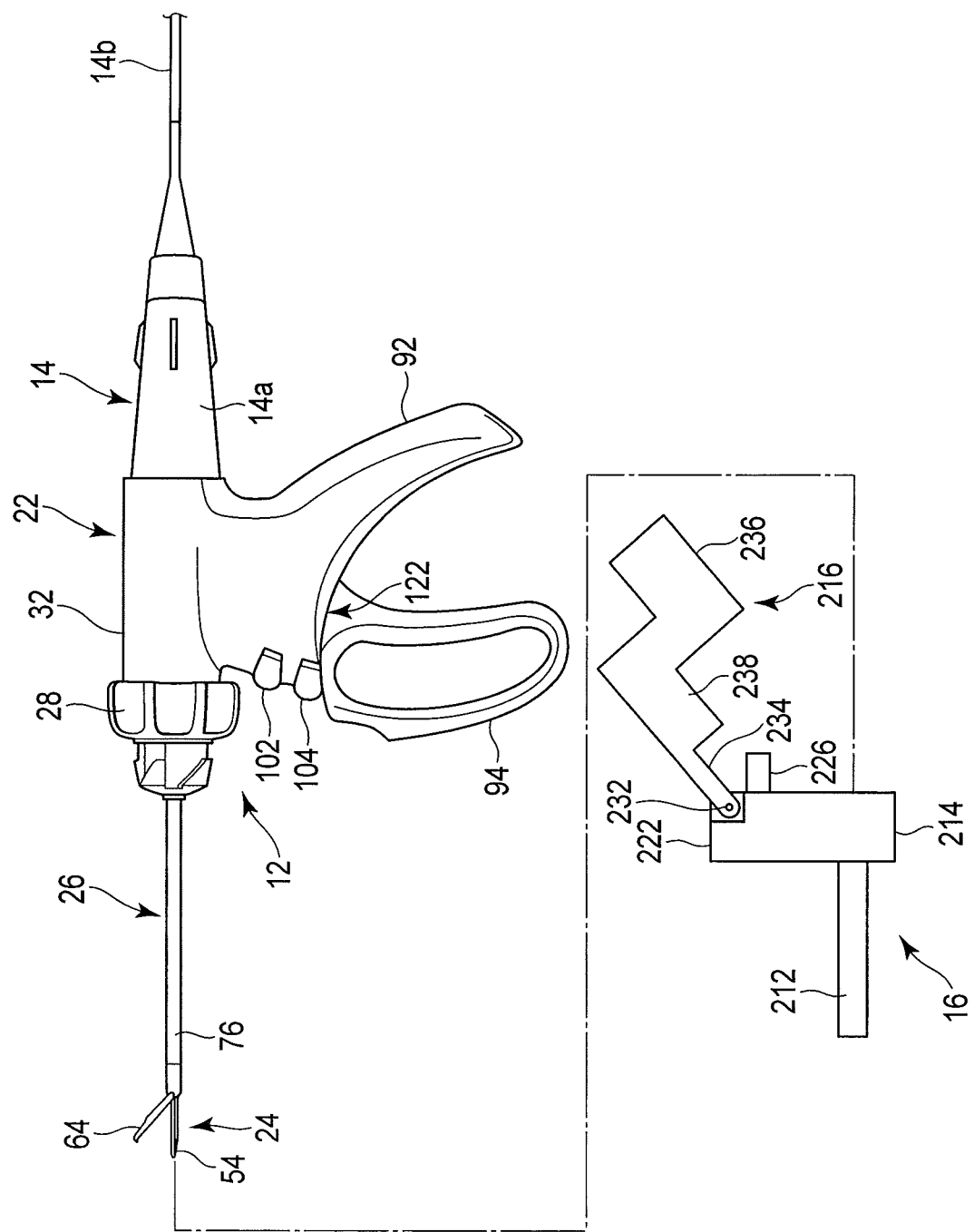
FIG. 5 is a schematic view showing the surgical treatment instrument and liquid feeder of the surgical operation system according to the first embodiment, and showing a state before the liquid feeder is attached to the surgical treatment instrument.

As shown in FIGS. 5 and 6, the liquid feeder 16 includes a main tube 212 which can be arranged along the sheath unit 26 on its outer circumference and can flow a liquid outside the sheath unit 26, a connection section 214 which is arranged on the proximal end side of the main tube 212 along the center axis C and connects the interior of the main tube 212 and the interior of a liquid feed tube 218 (see FIG. 1A) from the liquid source 20, and a fixing section (fixing tool) 216 which is arranged in the connection section 214 and fixes the connection section 214 to the handle unit 22. The liquid feed tube 218 is made of a flexible material. The main tube 212 may be made of a flexible material, similarly to the liquid feed tube 218, or made of a hard material such as a metal material or a hard plastic material.

As shown in FIG. 6, the connection section 214 includes an annular adapter 222 which is arranged outside the sheath unit 26, and a seal member 224 such as an O-ring which is arranged inside the annular adapter 222 and seals a portion with the outer circumferential surface of the sheath unit 26. Note that the seal member 224 can be elastically deformed, and is in tight contact with the outer circumferential surface of the sheath unit 26 to be slidable. The connection section 214 includes a connector 226 for connecting the liquid feed tube (liquid feed channel) 218 to the annular adapter 222. The annular adapter 222 includes a channel 228 for communicating the main tube 212 and the connector 226.

The fixing section 216 includes a hinge section 232 which is pivotable with respect to the connection section 214. As shown in FIG. 1A, the hinge section 232 allows the fixing section 216 to pivot between a solid-line position and a broken-line position.

As shown in FIG. 6, the fixing section 216 includes a pivotable arm 234 pivoted by the hinge section 232 on the annular adapter 222 of the connection section 214, and a holding section 236 held by the exterior case 32 of the handle unit 22. As shown in FIG. 1B, the cross section of the holding section 236 has an almost C shape, and is formed to be slightly smaller than the outside diameter of the exterior case 32 of the handle unit 22. That is, the holding section 236 of the fixing section 216 is used as a clamping section capable of clamping the handle unit 22.

As shown in FIG. 6, the hinge section 232 is formed at a position which does not influence the channel 228 of the annular adapter 222.

A guide section 238 for guiding the liquid feed tube 218 is provided between the proximal end of the arm 234 and the holding section 236. The guide section 238 is formed into a cylindrical shape.

Note that one end (proximal end) of the liquid feed tube 218 is connected to the connector 226 via the guide section 238, and other end (distal end) of the liquid feed tube 218 is connected to the liquid source 20.

The action of the surgical operation system 10 according to this embodiment will be described next.

A case in which the liquid feeder 16 shown in FIG. 5 is mounted on the surgical treatment instrument 12 in the state shown in FIG. 5 will be described first. More specifically, the liquid feeder 16 is mounted on the surgical treatment instrument 12 including
the long member in which the center axis (longitudinal axis) C is defined, that is, the probe 24 and/or the sheath unit 26, and the handle unit 22 arranged at the proximal end of the sheath unit 26 and grasped by the user.

The movable handle 94 is separated from the stationary handle 92. At this time, the jaw 64 arranged at the distal end of the sheath unit 26 is separated from the treatment section 54 at the distal end of the probe 24.

If the movable handle 94 is moved closer to the stationary handle 92, the jaw 64 is moved closer to the treatment section 54 of the probe 24 and is closed. In this state, the liquid feeder 16 is attached to the surgical treatment instrument 12. More specifically, the treatment section 54 and the jaw 64 are relatively moved from the proximal end side of the adapter 222 to the distal end side. At this time, the treatment section 54 and the jaw 64 are moved through the interior of the main tube 212. The proximal end of the annular adapter 222 then abuts against the distal end of the rotation knob 28. That is, the connection section 214 is arranged at a position closer to the distal end of the main tube 212 than the rotation knob 28. At this time, the jaw 64 and the treatment section 54 of the probe 24 project to the distal end side along the center axis C with respect to the distal end of the main tube 212 of the liquid feeder 16. In this example, the distal end of the sheath unit 26 projects to the distal end side, as compared with the distal end of the main tube 212. Furthermore, the fixing section 216 of the liquid feeder 16 is at the broken-line position in FIG. 1A.

The movable handle 94 is released. Then, the movable handle 94 is separated from the stationary handle 92 by the biasing force of the elastic member 144, and the jaw 64 opens with respect to the treatment section 54 of the probe 24.

The arm 234 of the liquid feeder 16 is moved closer to the exterior case 32 of the handle unit 22. Then, the holding section 236 of the liquid feeder 16 is elastically deformed to clamp and hold the exterior of the exterior case 32 of the handle unit 22 by the holding section 236 (see FIG. 1B).

The distal end (one end) of the liquid feed tube 218 is fixed to the connector 226 via the guide section 238 of the fixing section 216.

As described above, the surgical operation system 10 in the state in which the liquid feeder 16 is attached to the surgical treatment instrument 12 is appropriately used to treat a treatment target tissue.

When the rotation knob 28 is rotated about the center axis C, the sheath unit 26 including the jaw 64 and the probe 24 inside the sheath unit 26 are accordingly pivoted about the center axis C with respect to the main tube 212. At this time, the positions of the main tube 212, annular adapter 222, and fixing section 216 of the liquid feeder 16 with respect to the handle unit 22 are maintained. Thus, the position of the liquid feed tube 218 connected to the liquid feeder 16 remains unchanged with respect to the handle unit 22. Therefore, even if the rotation knob 28 is operated to rotate the sheath unit 26 and the probe 24, the liquid feed tube 218 maintains its position with respect to the handle unit 22. Consequently, the liquid feed tube 218 is prevented from winding about the handle unit 22, the transducer unit 14, the main tube 212 of the liquid feeder 16, or the like. Even if the knob 28 of the surgical treatment instrument 12 is rotated to appropriately rotate the sheath unit 26, the operability of the surgical treatment instrument 12 is prevented from being lowered.

If, for example, the upper switch 102 is pressed while the tissue is arranged (grasped) between the jaw 64 and the treatment section 54 of the probe 24, the tissue is coagulated and incised by Joule heat generated by high-frequency energy and the ultrasonic vibration. If, for example, the lower switch 104 is pressed while the tissue is arranged between the jaw 64 and the treatment section 54 of the probe 24, the tissue is heated and coagulated (if the tissue is a blood vessel, it is sealed) by Joule heat generated by high-frequency energy.

That is, by selectively pressing the upper switch 102 and the lower switch 104, a treatment function (for example, coagulation, incision, or the like) in the treatment section 54 of the probe 24 is selected.

When the upper switch 102 and the lower switch 104 are selectively pressed to treat the tissue, the controller 18 is controlled to supply a liquid such as physiological saline from the liquid source 20 to the liquid feeder 16 through the liquid feed tube 218. Then, the liquid is discharged from the distal end of the main tube 212 through the liquid source 20, the liquid feed tube 218, the connector 226 of the liquid feeder 16, the channel 228 in the adapter 222, and the main tube 212. At this time, the liquid enters between the tissue and the jaw 64 and between the tissue and the treatment section 54 of the probe 24. The liquid serves as a lubricant. Thus, the tissue is prevented from sticking to the jaw 64 and/or the treatment section 54 of the probe 24.

If treatment is performed to incise the tissue without supplying any liquid, the treated tissue tends to stick to the treatment section 54 of the probe 24. To the contrary, if treatment is performed while supplying a liquid, the liquid serves as a lubricant, and the tissue is difficult to stick to the treatment section 54, as compared with a case in which treatment is performed without supplying any liquid. Therefore, if treatment is performed while supplying a liquid, it is readily recognized that the treatment target tissue has been separated by incision.

When the tissue is treated by the ultrasonic vibration by pressing the upper switch 102, the temperature of the treatment section 54 of the probe 24 becomes high due to frictional heat with the tissue. By making the liquid contact the treatment section 54 of the probe 24, a rise in temperature of the treatment section 54 of the probe 24 is suppressed, as compared with a case in which no liquid is supplied.

In the surgical operation system 10 according to this embodiment, the probe 24 and sheath unit 26 of the surgical treatment instrument 12 and the main tube 212 of the liquid feeder 16 can be concentrically arranged. More specifically, the main tube 212 of the liquid feeder 16 can be arranged outside the sheath unit 26 of the surgical treatment instrument 12. Therefore, the user of the surgical operation system 10 need not arrange the surgical treatment instrument 12 and the liquid feeder 16 from different positions toward the treatment target tissue. That is, unlike a case in which a user (main operator) holds the surgical treatment instrument 12 and another user (assistant) holds the liquid feeder 16, a plurality of users need not appropriately move the surgical treatment instrument 12 and the liquid feeder 16 in cooperation with each other so as to maintain a desired positional relationship. If the user moves the surgical treatment instrument 12, the liquid feeder 16 can be moved together, thereby always maintaining the concentric positional relationship between the main tube 212 of the liquid feeder 16 and the probe 24 and sheath unit 26 of the surgical treatment instrument 12. Thus, the operator need not separately hold and move the surgical treatment instrument 12 and the liquid feeder 16 so as to maintain the desired positional relationship.

Therefore, in the surgical operation system 10 according to this embodiment, the treatment section 54 of the surgical treatment instrument 12 and the main tube 212 of the liquid feeder 16 can always be kept in a predetermined positional relationship. Consequently, by appropriately supplying a liquid such as physiological saline to the treatment section 54 through the main tube 212, the tissue between the jaw 64 and the treatment section 54 is prevented from sticking to, for example, the treatment section 54 and/or the jaw 64 as much as possible while suppressing a rise in temperature of the treatment section 54.

As described above, in the surgical operation system 10 according to this embodiment, when performing treatment while supplying a liquid such as physiological saline to the treatment section 54 of the probe 24, even if the orientation of the jaw 64 is adjusted to an appropriate one, it is possible to always maintain the positional relationship between the liquid feeder 16 and the handle unit 22 of the surgical treatment instrument 12 in the same state. It is thus possible to prevent the liquid feed tube 218 connecting the liquid source 20 and the liquid feeder 16 from winding around, for example, the handle unit 22 of the transducer unit 14, the transducer unit 14, or the main tube 212 of the liquid feeder 16 (the handle unit 22 or a member mounted on the handle unit 22). Therefore, it is possible to prevent the liquid feed tube 218 from winding around the surgical treatment instrument 12 and/or the transducer unit 14 during treatment, and maintain, in the predetermined state, the operability of the surgical treatment instrument 12 grasped by the user.

That is, the liquid feeder 16 mounted on the surgical treatment instrument 12 including the sheath unit (long member) 26 in which the center axis (longitudinal axis) C is defined and the handle unit 22 arranged at the proximal end of the sheath unit 26 and grasped by the user according to this embodiment includes the main tube 212 which is arranged on the outer circumference of the sheath unit 26 and can flow a liquid to the outer circumference of the sheath unit 26, the connection section 214 which is arranged on the proximal end side of the main tube 212 along the center axis C and connects the interior of the main tube 212 and the interior of the liquid feed tube (liquid feed channel) 218 from the liquid source 20, and the fixing section 216 which is arranged in the connection section 214 and fixes the connection section 214 to the handle unit 22.

The surgical operation system (treatment apparatus) 10 includes the surgical treatment instrument 12 including the sheath unit (long member) 26 in which the center axis (longitudinal axis) C is defined and the handle unit 22 arranged at the proximal end of the sheath unit 26 and grasped by the user, and the above-described liquid feeder 16 mounted on the surgical treatment instrument 12.

Note that an example in which the movable handle 94 is arranged on the front side with respect to the stationary handle 92 in the surgical treatment instrument 12 according to this embodiment has been explained. However, the movable handle 94 may be arranged on the rear side with respect to the stationary handle 92, as a matter of course.

Next, the first modification of the first embodiment will be described with reference to FIG. 7.

This modification is an example in which the fixing section 216 of the liquid feeder 16 and the outer circumferential surface of the exterior case 32 of the handle unit 22 of the surgical treatment instrument 12 are fixed by an adhesive or the like.

Even if the holding section 236 of the fixing section 216 of the liquid feeder 16 is fixed to the outer circumferential surface of the exterior case 32 of the handle unit 22 of the surgical treatment instrument 12 in this way, it is possible to perform treatment by combining the surgical treatment instrument 12 and the liquid feeder 16, as described in the first embodiment.

That is, the first embodiment assumes that the outer circumferential surface of the exterior case 32 is clamped by the holding section 236. As described in this modification, however, it is also preferable to hold a state in which the holding section 236 is in tight contact with the outer circumferential surface of the exterior case 32 by an adhesive or the like.

Next, the second modification of the first embodiment will be described with reference to FIG. 8.

This modification is an example in which the fixing section 216 of the liquid feeder 16 is hooked on the outer circumferential surface of the exterior case 32 of the handle unit 22 of the surgical treatment instrument 12.

Figure 8:
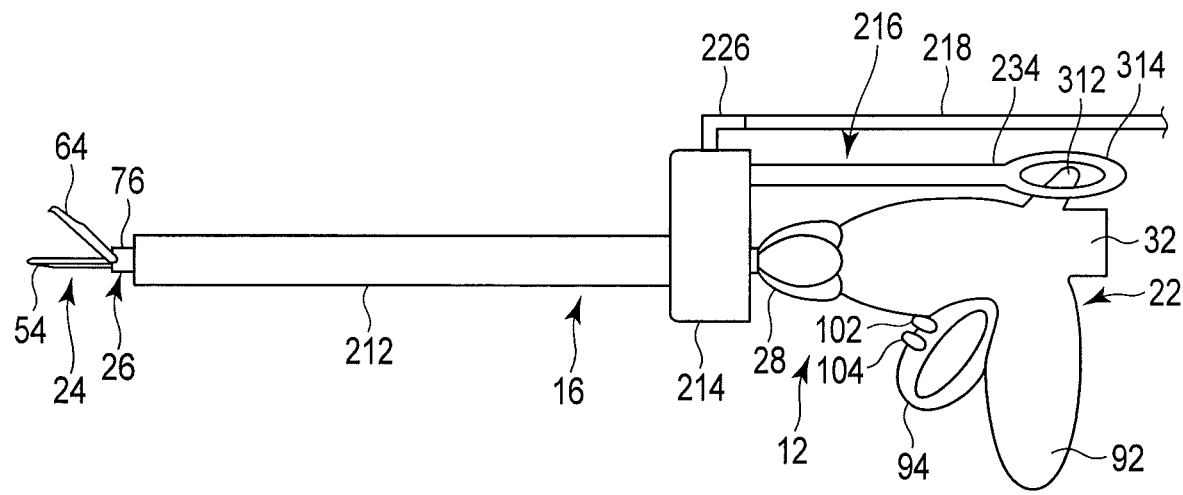
FIG. 8 is a schematic view showing the surgical treatment instrument and liquid feeder of the surgical operation system according to the second modification of the first embodiment, and showing a state in which the liquid feeder is attached to the surgical treatment instrument.

As shown in FIG. 8, a convex section (fixed section) 312 is formed at the proximal end of the exterior case 32. A hook section 314 which can be hooked on the convex section 312 is formed in the fixing section 216 of the liquid feeder 16. In this modification, the hook section 314 of the fixing section 216 is formed into a ring shape.

Even if the fixing section 216 of the liquid feeder 16 is hooked on the outer circumferential surface of the exterior case 32 of the handle unit 22 of the surgical treatment instrument 12 in this way, it is possible to perform treatment by combining the surgical treatment instrument 12 and the liquid feeder 16, as described in the first embodiment.

Next, the third modification of the first embodiment will be described with reference to FIG. 9.

This modification is an example in which the fixing section 216 of the liquid feeder 16 is hooked on the outer circumferential surface of the exterior case 32 of the handle unit 22 of the surgical treatment instrument 12.

Figure 9:
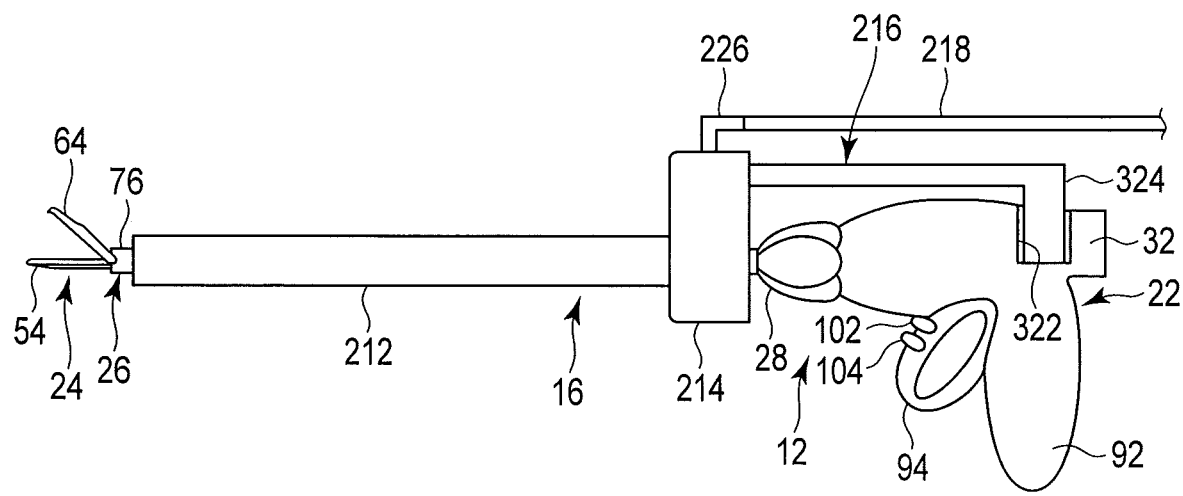
FIG. 9 is a schematic view showing the surgical treatment instrument and liquid feeder of the surgical operation system according to the third modification of the first embodiment, and showing a state in which the liquid feeder is attached to the surgical treatment instrument.

As shown in FIG. 9, a concave section (fixed section) 322 is formed at the proximal end of the exterior case 32. A hook section 324 which can be hooked on the concave section 322 is formed in the fixing section 216 of the liquid feeder 16. In this modification, the hook section 324 of the fixing section 216 is formed to be fitted in the concave section 322.

Even if the fixing section 216 of the liquid feeder 16 is hooked on the outer circumferential surface of the exterior case 32 of the handle unit 22 of the surgical treatment instrument 12 in this way, it is possible to perform treatment by combining the surgical treatment instrument 12 and the liquid feeder 16, as described in the first embodiment.

Next, the fourth modification of the first embodiment will be described with reference to FIG. 10.

This modification is an example in which the fixing section 216 of the liquid feeder 16 is hooked on the movable handle 94 of the handle unit 22 of the surgical treatment instrument 12.

Figure 10:
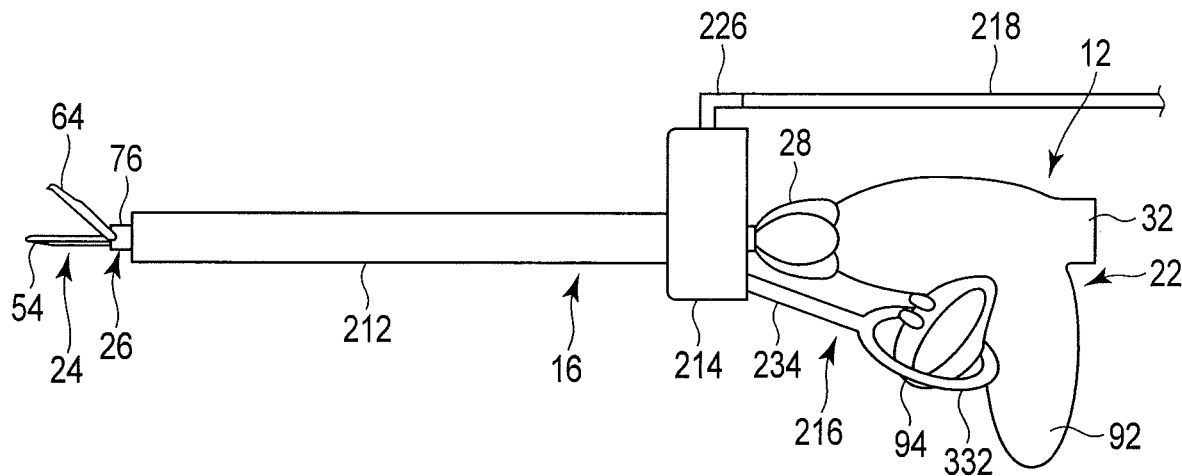
FIG. 10 is a schematic view showing the surgical treatment instrument and liquid feeder of the surgical operation system according to the fourth modification of the first embodiment, and showing a state in which the liquid feeder is attached to the surgical treatment instrument.

As shown in FIG. 10, a hook section 332 which can be hooked on the movable handle (fixed section) 94 is formed in the fixing section 216 of the liquid feeder 16. In this modification, the hook section 332 of the fixing section 216 is formed into a ring shape.

Even if the fixing section 216 of the liquid feeder 16 is hooked on the movable handle 94 of the handle unit 22 of the surgical treatment instrument 12 in this way, it is possible to perform treatment by combining the surgical treatment instrument 12 and the liquid feeder 16, as described in the first embodiment.

Figure 11:
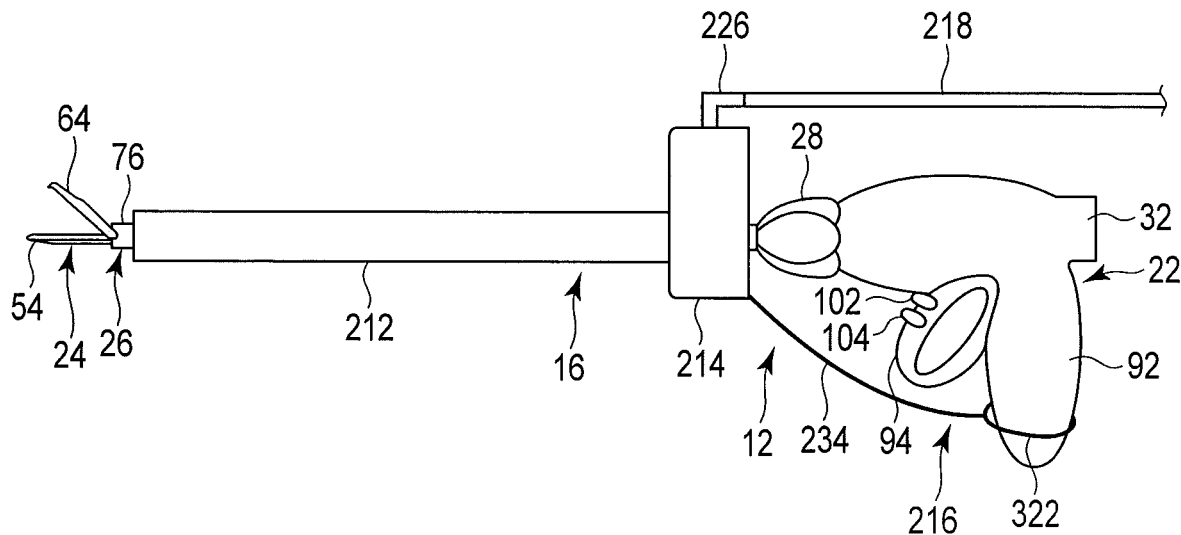
FIG. 11 is a schematic view showing the surgical treatment instrument and liquid feeder of the surgical operation system according to a modification of the fourth modification of the first embodiment, and showing a state in which the liquid feeder is attached to the surgical treatment instrument.

Note that as shown in FIG. 11, it is also preferable to hook the hook section 332 of the fixing section 216 of the liquid feeder 16 on the stationary handle (fixed section) 92 of the handle unit 22 of the surgical treatment instrument 12, as a matter of course.

That is, the hook section 332 of the fixing section 216 need only be supported by one of the stationary handle 92 and the movable handle 94.

Next, the fifth modification of the first embodiment will be described with reference to FIGS. 12A and 12B.

This modification is an example in which the distal end and proximal end of the handle unit 22 are sandwiched by the liquid feeder 16.

Figure 12A:
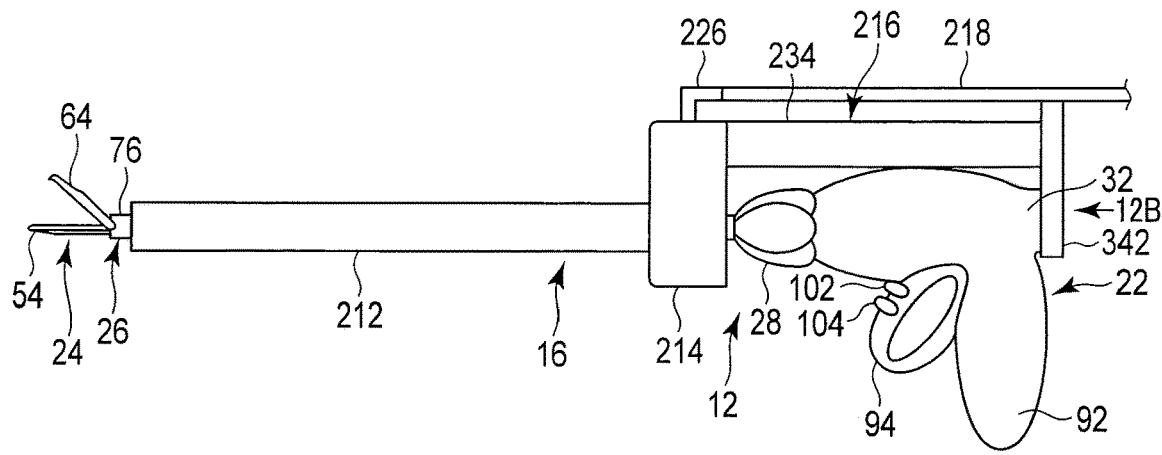
FIG. 12A is a schematic view showing the surgical treatment instrument and liquid feeder of the surgical operation system according to the fifth modification of the first embodiment, and showing a state in which the liquid feeder is attached to the surgical treatment instrument.
Figure 12B:
FIG. 12B is a schematic view showing a state when the surgical treatment instrument and the liquid feeder are viewed from the direction of an arrow 12B in FIG. 12A.

As shown in FIG. 12A, the adapter 222 of the liquid feeder 16 abuts against the distal end of the rotation knob 28. The fixing section 216 of the liquid feeder 16 includes a clamping body 342 for sandwiching the exterior case 32 of the handle unit 22 in cooperation with the adapter 222. As shown in FIG. 12B, the clamping body 342 includes an opening 342a in which the transducer unit 14 is disposed.

As described above, when the adapter 222 of the liquid feeder 16 and the clamping body 342 of the fixing section 216 clamp the distal end of the rotation knob 28 and the proximal end of the exterior case 32 of the handle unit 22, it is possible to perform treatment by combining the surgical treatment instrument 12 and the liquid feeder 16, as described in the first embodiment.

Next, the sixth modification of the first embodiment will be described with reference to FIGS. 13A and 13B.

This modification is an example in which the exterior of the exterior case 32 of the handle unit 22 is sandwiched by the fixing section 216 of the liquid feeder 16.

Figure 13A:
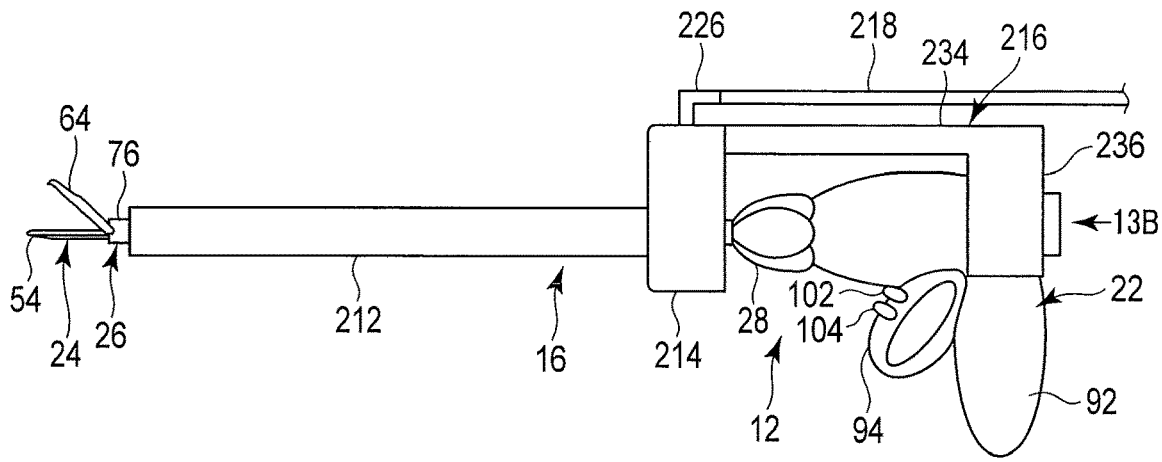
FIG. 13A is a schematic view showing the surgical treatment instrument and liquid feeder of the surgical operation system according to the sixth modification of the first embodiment, and showing a state in which the liquid feeder is attached to the surgical treatment instrument.
Figure 13B:
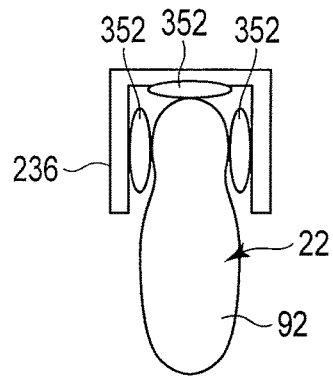
FIG. 13B is a schematic view showing a state when the surgical treatment instrument and the liquid feeder are viewed from the direction of an arrow 13B in FIG. 13A.

As shown in FIGS. 13A and 13B, one or a plurality of air bags 352 which press the exterior of the exterior case 32 of the handle unit 22 when air is inserted and release the pressure of the exterior of the exterior case 32 of the handle unit 22 when air is removed are arranged inside the holding section 236 of the fixing section 216 of the liquid feeder 16.

Note that tubes (not shown) which are connected to the air bags 352 to insert/remove air into/from them are preferably tied into a bundle together with the liquid feed tube 218. In this case, the tubes (not shown) and the liquid feed tube 218 are prevented from being tangled.

As described above, when air is inserted into the air bags 352 to press and clamp the exterior of the exterior case 32 of the handle unit 22 by the fixing section 216 of the liquid feeder 16, it is possible to perform treatment by combining the surgical treatment instrument 12 and the liquid feeder 16, as described in the first embodiment.

Next, the seventh modification of the first embodiment will be described with reference to FIGS. 14A and 14B.

This modification is an example in which the fixing section 216 of the liquid feeder 16 is plastically deformed to sandwich the exterior of the exterior case 32 of the handle unit 22.

Figure 14A:
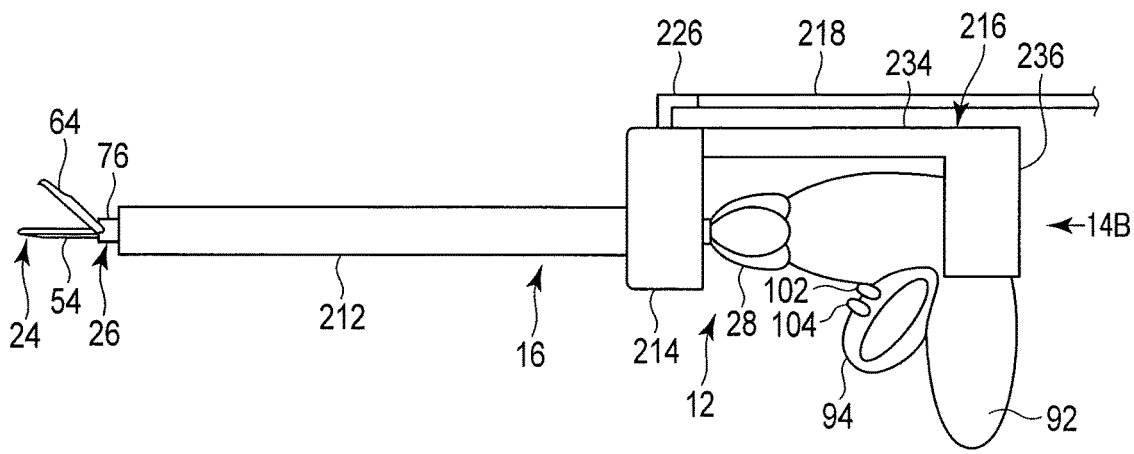
FIG. 14A is a schematic view showing the surgical treatment instrument and liquid feeder of the surgical operation system according to the seventh modification of the first embodiment, and showing a state in which the liquid feeder is attached to the surgical treatment instrument.
Figure 14B:
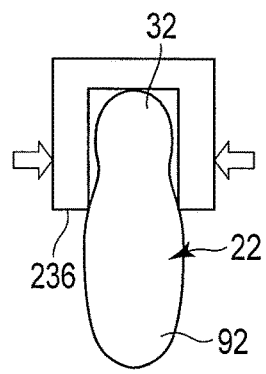
FIG. 14B is a schematic view showing a state when the surgical treatment instrument and liquid feeder are viewed from the direction of an arrow 14B in FIG. 14A.

A plastically deformable metal material is used for the holding section 236 of the fixing section 216 of the liquid feeder 16 shown in FIGS. 14A and 14B.

When the holding section 236 of the liquid feeder 16 is plastically deformed and the fixing section 216 of the liquid feeder 16 clamps the exterior of the exterior case 32 of the handle unit 22, that is, when the holding section 236 is fixed to the outer circumferential surface of the exterior case 32 by caulking, it is possible to perform treatment by combining the surgical treatment instrument 12 and the liquid feeder 16, as described in the first embodiment.

Note that when, instead of plastically deforming the holding section 236, the exterior of the exterior case 32 of the handle unit 22 is clamped by the fixing section 216 of the liquid feeder 16 using a material which is deformed by appropriately applying heat, that is, the holding section 236 is fixed to the outer circumferential surface of the exterior case 32 by heat deformation, it is also possible to perform treatment by combining the surgical treatment instrument 12 and the liquid feeder 16, as described in the first embodiment.

Next, the eighth modification of the first embodiment will be described with reference to FIG. 15.

This modification is an example in which magnets (magnetic bodies) 362 and 364 are arranged at the distal end of the rotation knob 28 and outside the exterior case 32 of the handle unit 22, respectively, and the magnetic forces of the pair of magnets 362 and 364 fix the liquid feeder 16 to the handle unit 22.

Figure 15:
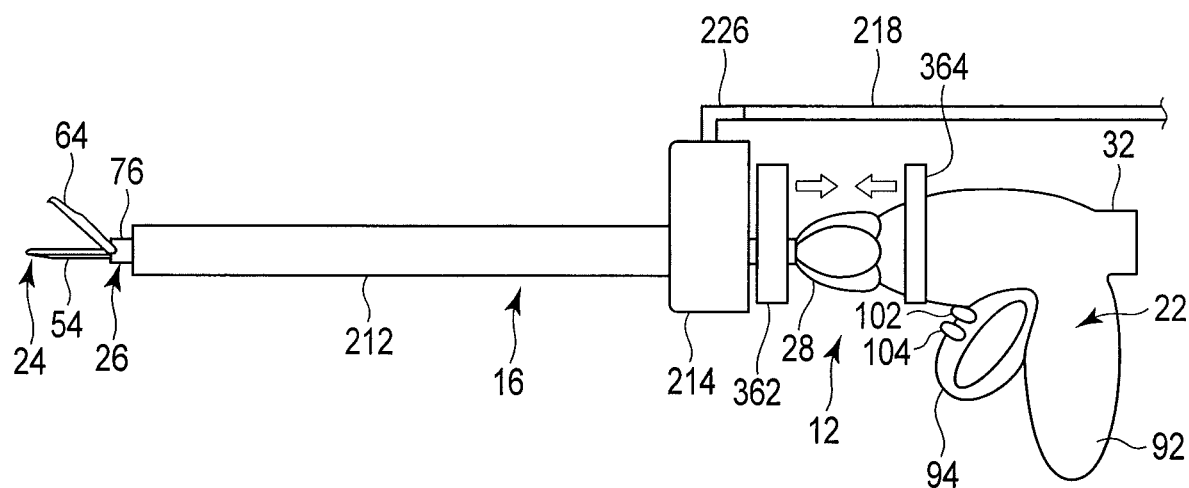
FIG. 15 is a schematic view showing the surgical treatment instrument and liquid feeder of the surgical operation system according to the eighth modification of the first embodiment, and showing a state in which the liquid feeder is attached to the surgical treatment instrument.
Figure 16:
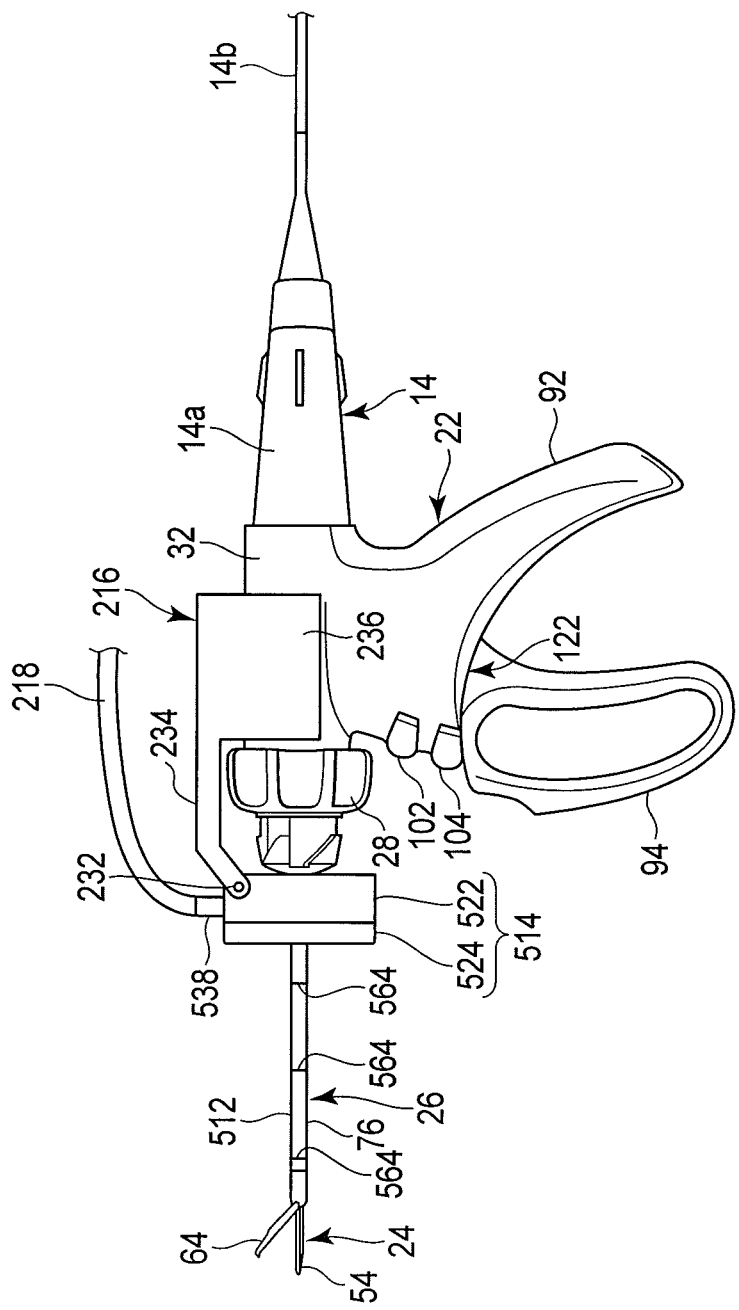
FIG. 16 is a schematic view showing the surgical treatment instrument and liquid feeder of a surgical operation system according to the second embodiment, and showing a state in which the liquid feeder is attached to the surgical treatment instrument.

As shown in FIG. 15, the first magnet 362 is arranged as a fixing section (fixing tool) at the proximal end of the adapter 222. The adapter 222 and the first magnet 362 are preferably integrated. The second magnet 364 is arranged as a fixing section (fixing tool) in the exterior case 32 of the handle unit 22. The first magnet 362 and the second magnet 364 are arranged to attract each other.

The magnetic forces of the first magnet 362 and the second magnet 364, which attract each other, can maintain the positional relationship between the adapter 222 and the exterior case 32 of the handle unit 22. Thus, by using the first magnet 362 and the second magnet 364, it is possible to perform treatment by combining the surgical treatment instrument 12 and the liquid feeder 16, as described in the first embodiment.

The second embodiment will be described with reference to FIGS. 16 to 18B. This embodiment is a modification of the first embodiment. The same members or members having the same functions as in the first embodiment including the respective modifications are denoted by the same reference numerals as much as possible and a detailed description thereof will be omitted.

A liquid feeder (water feeder) 416 shown in FIGS. 16 to 18B includes a main tube 512 which can be arranged on the outer circumference of a sheath unit 26 and extends outside the sheath unit 26, a connection section 514 which is arranged at the proximal end of the main tube 512 and connects the interior of the main tube 512 and the interior of a liquid feed tube 218 (see FIG. 1A) from a liquid source 20, and a fixing section (fixing tool) 216 which is arranged in the connection section 514 and fixes part of the connection section 514 to a handle unit 22.

As shown in FIG. 18A, the connection section 514 includes a fixing adapter 522 and a rotation adapter 524. Assume that the outer shape of each of the fixing adapter 522 and the rotation adapter 524 is a circular shape. However, any appropriate shape can be used.

The fixing adapter 522 includes an annular body 532, a through hole 534 which penetrates along a center axis C of the body 532, and an annular channel 536 concentrically formed with respect to the center axis C of the body 532. The body 532 has a distal end face 532a, a proximal end face 532b, and a side face 532c. The annular channel 536 is formed from the distal end face 532a of the body 532 toward its proximal end face 532b up to an appropriate depth but does not penetrate the proximal end face 532b. A connector 538 communicating with the annular channel 536 is disposed on the side face 532c of the body 532 of the fixing adapter 522.

The fixing adapter 522 is connected to the fixing section 216 described in the first embodiment. Therefore, if the fixing section 216 is fixed to an exterior case 32 of the handle unit 22, the fixing adapter 522 maintains a state in which it is positioned with respect to the handle unit 22.

The through hole 534 is formed to have an opening diameter slightly larger than the outside diameter of the sheath unit 26. If the fixing section 216 is fixed to the exterior case 32 of the handle unit 22, the sheath unit 26 and a probe 24 can freely rotate inside the through hole 534 of the fixing adapter 522.

The rotation adapter 524 can rotate about the center axis C with respect to the fixing adapter 522.

As shown in FIG. 18B, the rotation adapter 524 includes a body 542, a through hole 544, an annular convex section 546, and a channel 548. The body 542 has a distal end face 542a, a proximal end face 542b, and a side face 542c. The through hole 544 penetrates along the center axis C of the body 542. The annular convex section 546 is formed on the proximal end face 542b of the body 542. The channel 548 is formed in parallel to the center axis C of the body 542.

The through hole 544 is formed to have an opening diameter slightly larger than the outside diameter of the sheath unit 26. Seal members 552a and 552b such as O-rings are disposed on the inner circumferential surface of the through hole 544. The sheath unit 26 is supported by the seal members 552a and 552b inside the through hole 544 of the rotation adapter 524. Therefore, the rotation adapter 524 rotates along with the rotation of the sheath unit 26 and the probe 24.

Note that O-rings 554a and 554b are preferably arranged between the distal end face 532a of the body 532 of the fixing adapter 522 and the proximal end face 542b of the body 542 of the rotation adapter 524. Furthermore, O-rings 556a and 556b are preferably arranged between the annular channel 536 and the inner and outer circumferential surfaces of the annular convex section 546.

The annular convex section 546 can be fitted in the annular channel 536 of the fixing adapter 522. The channel 548 penetrates between a proximal end face 546a of the annular convex section 546 and the distal end face 542a of the body 542.

As shown in FIG. 18A, a connector 558 communicating with the channel 548 is formed on the distal end face of the rotation adapter 524. The proximal end of the main tube 512 is connected to the connector 558. The distal end of the main tube 512 is opened near the distal end of an outer sheath 76 of the sheath unit 26.

Note that the main tube 512 is drawn in a shape extending along the outer circumferential surface of the sheath unit 26.

However, the main tube 512 is also preferably formed to cover the entire outer circumference of the sheath unit 26, that is, like the main tube 212 described in the first embodiment.

For example, pinch bodies 564 elastically deformable in a C shape are arranged at appropriate intervals in the main tube 512. The pinch bodies 564 are elastically deformed to hold the outer circumferential surface of the sheath unit 26.

The action of a surgical operation system 10 according to this embodiment will be described next.

Figure 17:
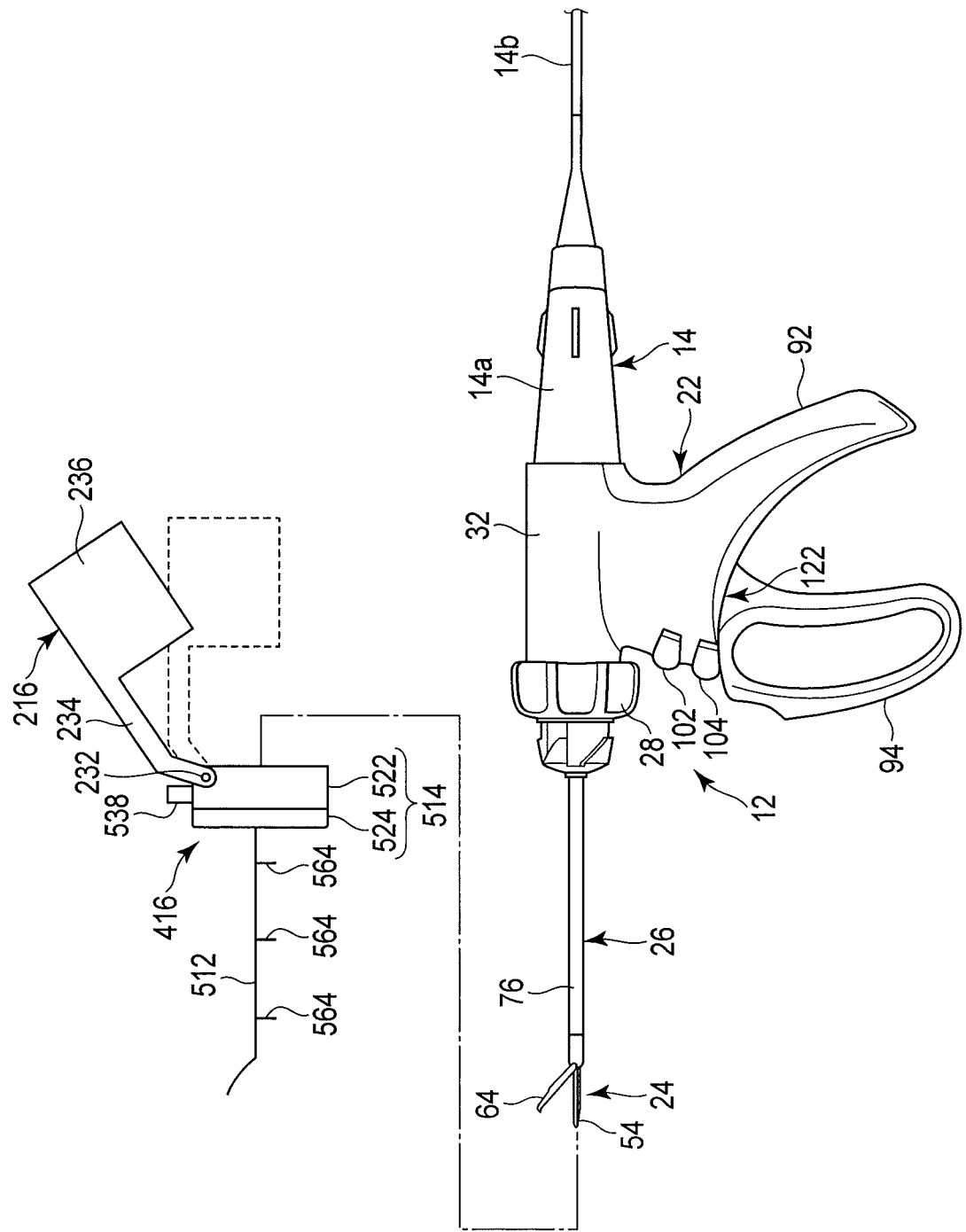
FIG. 17 is a schematic view showing the surgical treatment instrument and liquid feeder of the surgical operation system according to the second embodiment, and showing a state before the liquid feeder is attached to the surgical treatment instrument.

A case in which the liquid feeder 416 shown in FIG. 17 is mounted on a surgical treatment instrument 12 shown in FIG. 17 will be described first.

A movable handle 94 is moved closer to a stationary handle 92 to close a jaw 64 with respect to a treatment section 54 of the probe 24. In this state, the liquid feeder 416 is attached to the surgical treatment instrument 12. More specifically, the treatment section 54 and the jaw 64 are relatively moved from the proximal end side of the connection section 514 to the distal end side.

The proximal end of the fixing adapter 522 of the connection section 514 abuts against the distal end of a rotation knob 28. At this time, the seal members 552a and 552b inside the rotation adapter 524 of the connection section 514 are in tight contact with the outer circumferential surface of the outer sheath 76.

Then, the movable handle 94 is released. Accordingly, the movable handle 94 is separated from the stationary handle 92 by the biasing force of the elastic member 144, and the jaw 64 opens with respect to the treatment section 54 of the probe 24.

An arm 234 of the liquid feeder 416 is moved closer to the exterior case 32 of the handle unit 22. The holding section 236 of the liquid feeder 416 is elastically deformed to clamp and hold the exterior of the exterior case 32 of the handle unit 22 by the holding section 236 (see FIG. 16).

The distal end (one end) of the liquid feed tube 218 is fixed to the connector 538 of the connection section 514 of the liquid feeder 416.

On the other hand, the circumferential-direction position of the connector 558 of the rotation adapter 524 of the liquid feeder 416 with respect to the sheath unit 26 is set to an appropriate position. The proximal end of the main tube 512 is attached to the connector 558. The pinch bodies 564 clamp the outer circumference of the outer sheath 76 of the sheath unit 26. Therefore, the opening at the distal end of the main tube 512 is arranged at a position near the distal end of the outer sheath 76 of the sheath unit 26.

As described above, the surgical operation system 10 in the state in which the liquid feeder 416 is attached to the surgical treatment instrument 12 is appropriately used to treat a treatment target tissue.

When the rotation knob 28 is rotated about the center axis C, the sheath unit 26 including the jaw 64 and the probe 24 inside the sheath unit 26 are accordingly pivoted about the center axis C. At this time, since the rotation adapter 524 is in tight contact with the seal members 552a and 552b, the rotation adapter 524 and the main tube 512 rotate along with the rotation of the outer sheath 76. At this time, the positions of the fixing section 216 and the fixing adapter 522 of the liquid feeder 416 with respect to the handle unit 22 are maintained. Therefore, the position of the liquid feed tube 218 connected to the liquid feeder 416 remains unchanged with respect to the handle unit 22. Even if, therefore, the rotation knob 28 is operated to rotate the sheath unit 26 and the probe 24, the liquid feed tube 218 maintains its position with respect to the handle unit 22. Thus, the liquid feed tube 218 is prevented from winding around the handle unit 22, the transducer unit 14, or the sheath unit 26 attached with the main tube 512.

As described in the first embodiment, when a treatment target tissue is treated by appropriately operating switches 102 and 104, while controlling the liquid source 20 by a controller 18, the surgical operation system 10 according to this embodiment discharges a liquid from the distal end of the main tube 212 through the liquid source 20, the liquid feed tube 218, the connector 538 of the liquid feeder 416, the annular channel 536 in the fixing adapter 522, and the channel 548 and the main tube 512 in the rotation adapter 524.

Thus, by making the liquid contact the treatment section 54 of the probe 24, a rise in temperature of the treatment section 54 of the probe 24 is suppressed, as compared with a case in which no liquid is supplied.

In the surgical operation system 10 according to this embodiment, it is possible to always rotate the probe 24 and sheath unit 26 of the surgical treatment instrument 12 and the main tube 512 of the liquid feeder 416 at the same time. Therefore, the user of the surgical operation system 10 need not arrange the surgical treatment instrument 12 and the liquid feeder 416 from different positions toward the treatment target tissue. That is, unlike a case in which a user (main operator) holds the surgical treatment instrument 12 and another user (assistant) holds the liquid feeder 416, a plurality of users need not appropriately move the surgical treatment instrument 12 and the liquid feeder 416 in cooperation with each other so as to maintain a desired positional relationship. If the user moves the surgical treatment instrument 12, the liquid feeder 416 can be moved together, and the main tube 512 of the liquid feeder 416 and the probe 24 and sheath unit 26 of the surgical treatment instrument 12 can always maintain the same positional relationship. Thus, the operator need not separately hold and move the surgical treatment instrument 12 and the liquid feeder 416 so as to maintain the desired positional relationship.

Therefore, in the surgical operation system 10 according to this embodiment, the treatment section 54 of the surgical treatment instrument 12 and the main tube 512 of the liquid feeder 416 can always be kept in a predetermined positional relationship. Consequently, by appropriately supplying a liquid such as physiological saline to the treatment section 54 through the main tube 512, the tissue between the jaw 64 and the treatment section 54 is prevented from sticking to, for example, the treatment section 54 and/or the jaw 64 as much as possible while suppressing a rise in temperature of the treatment section 54.

As described above, in the surgical operation system 10 according to this embodiment, when performing treatment while supplying a liquid such as physiological saline to the treatment section 54 of the probe 24, even if the orientation of the jaw 64 is adjusted to an appropriate one, it is possible to always maintain the positional relationship between the liquid feeder 416 and the handle unit 22 of the surgical treatment instrument 12 in the same state. It is thus possible to prevent the liquid feed tube 218 connecting the liquid source 20 and the liquid feeder 416 from winding around, for example, the handle unit 22 of the transducer unit 14, the transducer unit 14, or the main tube 512 of the liquid feeder 416 (the handle unit 22 or a member mounted on the handle unit 22). Therefore, it is possible to prevent the liquid feed tube 218 from winding around the surgical treatment instrument 12 and/or the transducer unit 14 during treatment, and maintain, in the predetermined state, the operability of the surgical treatment instrument 12 grasped by the user.

Note that when fixing the liquid feeder 416 according to this embodiment to the handle unit 22 of the surgical treatment instrument 12, it is possible to fix it, as described in each modification of the first embodiment, as a matter of course.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A liquid feeder mounted on a treatment instrument including an elongate member with a longitudinal axis, a handle arranged at a proximal end of the elongate member, and a rotation knob arranged at a distal end of the handle and configured to rotate the elongate member about the longitudinal axis, the liquid feeder comprising:
   a main tube disposed along the elongate member and configured to flow a liquid to an outer circumference of the elongate member;
   a connection section disposed on a proximal end side of the main tube, the connection section including a connector connected to a fist end of a liquid feed tube, a second end of the liquid feed tube being connected to a liquid source, and the connection section is configured to connect an interior of the main tube with an interior of the liquid feed tube via the connector;
   a seal member disposed inside the connection section and configured to form a watertight seal between the connection section and the elongate member; and
   a fixing section rotatably attached to a proximal end of the connection section, the fixing section, the fixing section being configured to: pivot with respect to the connection section into a fixed position relative to the handle, the connection section being disposed at a distal end of the rotation knob, and
      maintain an orientation of the connection section with respect to the handle when the fixing section is in the fixed position and while the elongate member of the treatment instrument is rotated about the longitudinal axis with respect to the handle.

2. The liquid feeder of claim 1, wherein the connection section includes:
   a fixing adapter in which the connector connected to the liquid feed tube is disposed and an annular channel communicating with the connector is formed, the fixing adapter being fixed to the handle together with the fixing section, and
   a rotation adapter connected to the main tube, the rotation adapter being configured to form a channel communicating with the annular channel of the fixing adapter by being connected to the fixing adapter, and the rotation adapter is configured to rotate along with rotation of the rotation knob and the elongate member.

3. The liquid feeder of claim 1, further comprising a pinch body configured to clamp the outer circumference of the elongate member and disposed in the main tube.

4. The liquid feeder of claim 1, wherein the fixing section includes a clamping section configured to clamp the handle.

5. The liquid feeder of claim 1, wherein the fixing section is rotatably attached to the connection section by a hinge.

6. The liquid feeder of claim 1, wherein the liquid feed tube is not rotatable with respect to the handle when the rotation knob is rotated.

7. A treatment apparatus comprising: the liquid feeder of claim 1; and the treatment instrument including the elongate member in which the longitudinal axis is defined, the handle arranged at the proximal end of the elongate member, and the rotation knob arranged at the distal end of the handle and configured to rotate the elongate member about the longitudinal axis, wherein the liquid feeder is mounted on the treatment instrument.

8. The treatment apparatus of claim 7, wherein the elongate member includes a sheath disposed along the elongate member and extending beyond a distal end of the main tube.

9. The treatment apparatus of claim 7, wherein the elongate member includes:
   a sheath disposed along the elongate member and extending beyond a distal end of the main tube,
   a probe configured to transmit an ultrasonic vibration, the probe including an outer circumference covered with the sheath, and
   a jaw disposed at a distal end of the sheath, the jaw being configured to contact and separate from a distal end of the probe.

10. The treatment apparatus of claim 7, wherein the handle includes a fixed section to which the fixing section is fixed.

* * * * *